(12) United States Patent
Wen

(10) Patent No.: US 6,520,911 B1
(45) Date of Patent: Feb. 18, 2003

(54) ULTRASOUND-HALL EFFECT IMAGING SYSTEM AND METHOD

(75) Inventor: Han Wen, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/202,459

(22) PCT Filed: Jul. 2, 1997

(86) PCT No.: PCT/US97/11272

§ 371 (c)(1),
(2), (4) Date: May 11, 1999

(87) PCT Pub. No.: WO98/00732

PCT Pub. Date: Jan. 8, 1998

Related U.S. Application Data

(60) Provisional application No. 60/021,204, filed on Jul. 3, 1996.

(51) Int. Cl.[7] ................................................. A61B 8/00
(52) U.S. Cl. ...................................................... 600/437
(58) Field of Search ..................... 175/40, 50; 181/106; 73/105; 600/437, 438, 442, 407, 443, 587; 324/226, 228, 260

(56) References Cited

U.S. PATENT DOCUMENTS

| 4,001,773 A | * | 1/1977 | Lamel et al. ................. 175/40 |
| 4,149,421 A | | 4/1979 | Bottcher et al. |
| 4,449,408 A | | 5/1984 | Brooks et al. |
| 4,449,411 A | | 5/1984 | Suhr et al. |
| 4,689,996 A | | 9/1987 | Huschelrath |
| 5,131,392 A | | 7/1992 | Jolesz et al. |
| 5,146,924 A | | 9/1992 | Sepponen |
| 5,164,921 A | | 11/1992 | Graff et al. |
| 5,275,165 A | | 1/1994 | Ettinger et al. |
| 5,279,160 A | | 1/1994 | Koch |
| 5,402,786 A | | 4/1995 | Drummond |
| 5,421,203 A | | 6/1995 | Graff et al. |
| 5,436,873 A | | 7/1995 | MacLauchlan et al. |

OTHER PUBLICATIONS

A.H. Thompson & G.A. Gist: "Geophysical Applications of Electrokinetic Conversion", The Leading Edge, vol. 12, No. 12, 1993, of Exploration Geophysicists US, pp. 1169–1173, XP002045525.

Roth B J et al: "A Theoretical Model for Magneto–Acoustic Imaging of Bioelectric Currents", IEEE Transactions on Biomedical Engineering, vol. 41, No. 8, Aug. 1994, pp. 723–728, ISSN 0018–9294, XP002045524.

Database Inspec Institute of Electrical Engineers, Stevenage, GB Inspec No. 2397905, Chamuel J R: "Four Novel Nondestructive Evaluation Techniques" XP002045526.

Review of Progess in Quantitative Nondestructive Evaluation, vol. 3, Proceedings of the Tenth Annual Review, Santa Cruz, CA, USA, 7–12, Aug. 1983, 1984, New York, NY, USA, Plenum, USA, pp. 863–870.

* cited by examiner

Primary Examiner—George Manuel
(74) Attorney, Agent, or Firm—Leydig, Voit & Mayer, Ltd.

(57) ABSTRACT

A system and method of imaging based on the interaction of ultrasonic pulses with a magnetic field. A static magnetic field is applied to an object having conductive properties. An ultrasound pulse is propagated into the object, and an electrical signal is detected which is related to the interaction of the ultrasound pulse local displacement of the conductive object and the magnetic field. Alternatively, and equivalently, an electrical pulse is propagated into the object, and an ultrasound signal is detected which is related to the interaction of the electrical pulse generated in the conductive object and the magnetic field. The acquired acoustic signals or the acquired electrical signals are processed to provide an image of the object. The acquired signals are dependent on local conductivity as well as local acoustic properties.

39 Claims, 12 Drawing Sheets

Spatial domain

- - - - - - - - - - - - - - - - - - - - - - - -

Time domain

Magnitude HEI Image

Photograph FIG. 6A
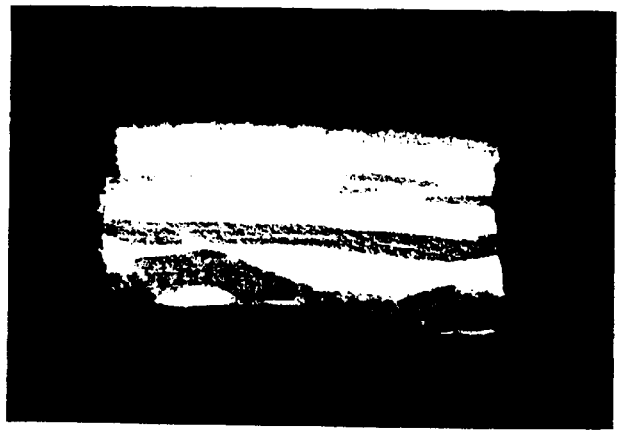
Hall Effect Image FIG. 6B
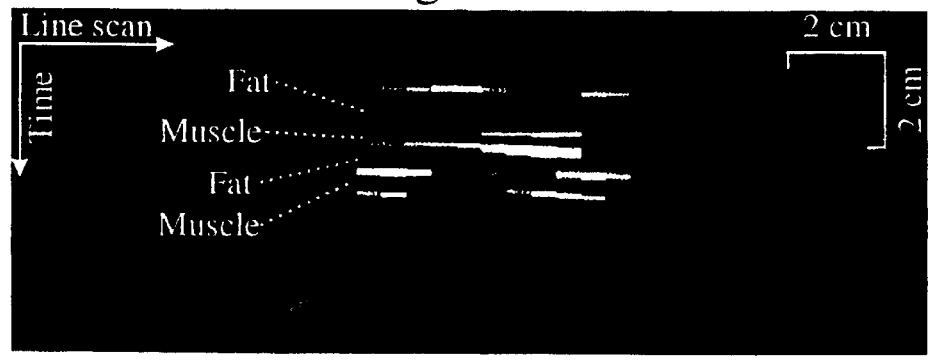
Echo Ultrasound Image FIG. 6C
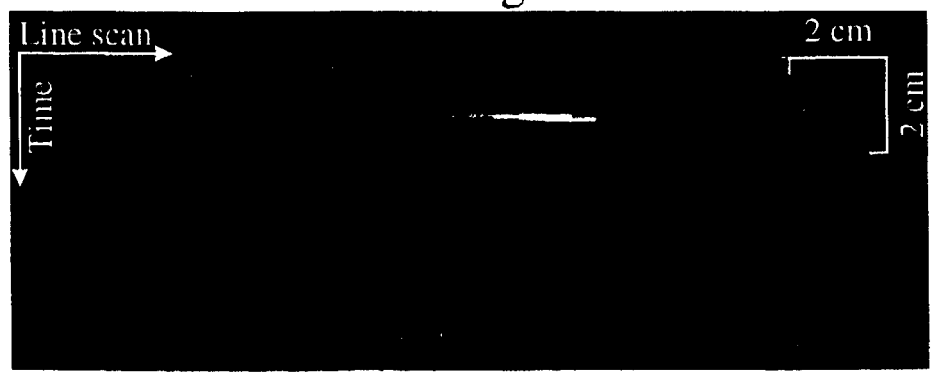

ULTRASOUND-HALL EFFECT IMAGING SYSTEM AND METHOD

This application claims the benefit of Provisional application Ser. No. 60/021,204, filed Jul. 3, 1996.

TECHNICAL FIELD

The present invention relates generally to ultrasound imaging, and more particularly to an imaging method and system based on the interaction of ultrasound pulses with a static magnetic field, preferably used to image the human body.

BACKGROUND OF THE INVENTION

Conventional ultrasound imaging techniques rely essentially only on the acoustic properties of the object or subject being imaged as the basic contrast mechanism for producing an image. Specifically, in such conventional ultrasonic imaging the progression of the pulse is monitored by detecting the echoes of the pulse reflected back at the tissue—tissue interfaces, and is therefore entirely a characterization of the acoustic impedances of the tissues. The acoustic path involved starts from the transducer that generates the ultrasonic pulse, reaches the tissue—tissue interfaces, and back to the transducer if it is also used to receive the echoes, or to another receiving transducer. The overall efficacy of such conventional ultrasound techniques is often hindered by the limited sizes of the acoustic windows in the body. Moreover, there is an inherent problem of beam expansion and low angular resolution away from the origin of the beam in these conventional ultrasound imaging methods.

Thus, although conventional ultrasound techniques provide a very useful imaging modality, further advancements in ultrasound techniques would be advantageous, particularly to provide an improved ultrasound-based imaging method which is not limited to contrast based solely on acoustic impedance, is not limited by beam expansion, and is not limited by the sizes of acoustic windows.

SUMMARY OF THE INVENTION

It is, therefore, an object of the present invention to provide a new ultrasound-based imaging modality.

A related object of the present invention is to provide a new ultrasound-based imaging modality that is based on the interaction among a static magnetic field and conductive moieties or media having a motion or displacement that is associated with acoustic energy.

Another object of the present invention is to provide a new ultrasound-based imaging modality that provides a contrast mechanism which includes the conductivity of the medium being imaged.

The present invention achieves these and other objects, and overcomes the above mentioned and other limitations of the prior art, by providing a method and system for imaging a subject or object having conductive properties, such that a static magnetic field is applied to the object or subject, and an ultrasound pulse is propagated into the object, and an electrical signal is detected which is related to the interaction of the ultrasound pulse local displacement of the conductive object and the magnetic field. Alternatively, and equivalently, a static magnetic field is applied to the object or subject, an electrical pulse is propagated into the object, and an ultrasound signal is detected which is related to the interaction of the electrical pulse generated in the conductive object and the magnetic field. The acquired acoustic signals or the acquired electrical signals are processed to provide an image of the object. The acquired signals are dependent on local conductivity as well as local acoustic properties. Imaging in accordance with the present invention is hereinafter also referred to as ultrasound-Hall effect imaging or Hall effect imaging (HEI).

BRIEF DESCRIPTION OF THE DRAWINGS

Additional aspects, features, and advantages of the invention will be understood and will become more readily apparent when the invention is considered in the light of the following description made in conjunction with the accompanying drawings, wherein:

FIG. 6A is a photograph of the cross section of a block of bacon used with the experimental setup of FIG. 5A, in accordance with the present invention;

FIG. 6B is an image of the bacon of FIG. 6A generated by HEI using the experimental setup of FIG. 5A, in accordance with the present invention; and FIG. 6C is a conventional echo ultrasound image of the block of bacon of FIG. 6A.

DETAILED DESCRIPTION OF THE PREFERRED EMBODIMENT

Figure 1A:
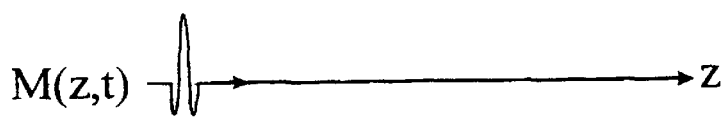
FIG. 1A depicts an ultrasound wave packet propagating along the Z axis, carrying the momentum M(z, t) through a sample, in accordance with an illustration of principles of the present invention.

Before further describing embodiments for, and examples of, practicing the present invention, principles applicable to the present invention are described. The present invention is directed to a system and method to form an image of a conductive subject, such as the human body. The method/system has two basic implementations or embodiments.

The first implementation is based on the fact that when a conductive subject moves in a direction perpendicular to an external magnetic field, the positive and negative charge carriers in the subject experience the Lorentz force in opposite directions and therefore tend to separate, the separation of charge giving rise to an electric field that emanate from the region of positive charge concentration and terminates at the region of negative charge concentration. This electric field can be detected in the form of a voltage difference between the positive region and the negative region, the Hall voltage. The separation of the positive and negative charge is equivalent to an electric current, the Hall current, which can also be detected via wire loops that are inductively coupled to the subject. The magnitude and phase of the Hall voltage and Hall current are dependent on the velocity of the movement of the subject and its conductivity and dielectric constant.

More particularly, if an ultrasound pulse is generated at the surface of the subject and propagates into the subject, wherever the pulse is currently located, the conductive medium at that location vibrates with the pulse. If the motion of the vibration is perpendicular to an external magnetic field, a Hall voltage and Hall current can be detected as described above. The magnitude and phase of the Hall signal is dependent on the vibrational velocity and therefore the acoustic impedance of the medium at that location, as well as the charge carrier density and mobility and therefore the conductivity and dielectric constant at that location.

Therefore by continuously monitoring the Hall signal while the ultrasound pulse travels through the subject, an image of the portion of the subject along the path of the ultrasound pulse can be formed based on the electrical constants and the acoustic impedance. If the ultrasound path is swept through a series of directions, a two-dimensional or three-dimensional image can be formed.

A second, and essentially physically equivalent, basic implementation is based on the fact that in the presence of a magnetic field, if a subject carries a current that is perpendicular to the direction of the magnetic field, the subject experiences a Lorentz force in the direction perpendicular to the plane formed by the vector of the magnetic field and the vector of the current. Therefore, in the presence of a static magnetic field, if a current distribution is induced in the bulk of a subject either through direct contact with electrodes or inductive coupling, and in the form of a short pulse in time, the bulk of the subject will experience a Lorentz force in the form of a short pulse, and will vibrate under this force. The vibration from a region in the subject reaches the surface of the subject at a time proportional to the acoustic path length between the region and the surface, and the amplitude of the vibration is dependent on the electric constants and acoustic impedance of that region. By sensing these vibrations with an acoustic transducer at the surface of the subject, which arrive in sequence according to the depths of the regions from which they originate, a one-dimensional image can be formed along the sensitive beam of the transducer. This image carries information on the electric constants as well as the acoustic impedances along that beam. Two-dimensional and three-dimensional images can be formed by using an array of sensing transducers simultaneously, or by sweeping the sensitive beam of a transducer over a range of directions.

Based on applying the electro-mechanical reciprocity relation, the above two implementations produce identical images of the subject. Each implementation can be applied to imaging the human body. The tissues of the body have different conductivity constants and dielectric constants. The contrast of the images acquired with the above methods are based on the electric constants of tissues, therefore they display the anatomy of the body. They also provide medical diagnostic information, that are related to the electrical properties of tissues, such as ionic concentration.

Figure 1B:
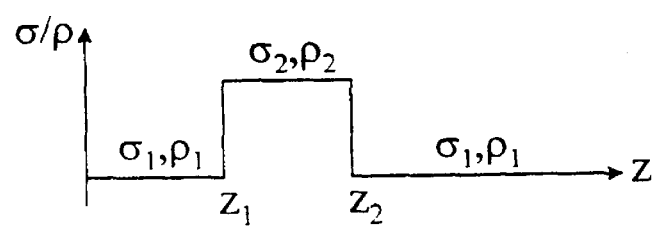
FIG. 1B shows the ratio of conductivity σ to mass density ρ along the Z axis in the sample through which the ultrasound wave packet of FIG. 1A propagates, in accordance with an illustration of principles of the present invention.

To further illustrate the dependence of the Hall voltage on the electrical and acoustic properties of the sample, consider a one-dimensional example illustrated in FIGS. 1A–D. An ultrasound transducer generates a longitudinal wave packet along the "Z" axis (FIG. 1A) perpendicular to a magnetic field $B_0$ (not shown). A step change in conductivity $\sigma$ and mass density $\rho$ occurs between positions $z_1$ and $Z_2$ (FIG. 1B). If the velocity of the ultrasound vibration at position z and time t is v(z, t), a charge q at that position experiences a Lorentz force $qv(z, t)B_0$. This force is equivalent to that of an electric field $v(z, t)B_0$, which in turn establishes a current density $\sigma(z)v(z, t)B_0$ in the sample. The net current derives from integrating this over the ultrasound beam width W and the ultrasound path:

$$I(t) = WB_0 \int_{soundpath} \sigma(z)v(z, t)dz. \tag{1}$$

If a portion $\alpha$ of the current is collected by electrodes into a detection circuit of impedance $R_d$, the detected Hall voltage $V_h(t)$ is then $$V_h(t) = \alpha R_d WB_0 \int_{soundpath} \sigma(z)v(z, t)dz. \tag{2}$$

Using the equation of wave propagation, the Hall voltage can be expressed in terms of the ultrasound momentum M(z,t) and the spatial gradient of $\sigma/\rho$. More particularly, denoting the ultrasound pressure wave as p(z, t), by using the equation of sound propagation:

$$\rho(z)\frac{\partial v(z, t)}{\partial t} + \frac{\partial p(z, t)}{\partial z} = 0 \tag{3}$$

the Hall voltage in equation (2) can be expressed as:

$$V_h(t) = -\alpha W R_d B_0 \int_{soundpath} \frac{\sigma(z)}{\rho(z)} \left[ \int_{-\infty}^{t} \frac{\partial p(z,\tau)}{\partial z} d\tau \right] dz \qquad (4)$$

Integration by parts yields:

$$V_h(t) = \qquad (5)$$
$$\alpha W R_d B_0 \int_{soundpath} \frac{\partial}{\partial z} \left[ \frac{\sigma(z)}{\rho(z)} \right] M(z,t) dz - \frac{\sigma(z)}{\rho(z)} M(z,t) \Big|_{soundpathbeginning}^{soundpathend}$$

where $$M(z,t) = \int_{-\infty}^{t} \frac{\partial p(z,\tau)}{\partial z} d\tau \qquad (6)$$

is the ultrasound momentum transmitted across position z at time t. Practical ultrasound transducers emit little energy in the audio and DC frequency range. The lack of a DC component means that the net momentum of the wave packet is zero. Under this condition, it can be shown that the surface term in equation (6) is zero during the time the wave packet is somewhere within the ultrasound path. Hence the Hall voltage can be expressed as:

$$V_h(t) = \alpha W R_d B_0 \int_{soundpath} M(z,t) \frac{\partial}{\partial z} \left[ \frac{\sigma(z)}{\rho(z)} \right] dz. \qquad (7)$$

This expression shows that a non-zero Hall voltage only comes from positions where a gradient of $\sigma/\rho$ exists. This point can be visualized by observing the total Hall effect (HE) current in equation (1), while following the progression of the ultrasound wave packet. When the wave packet is in a homogeneous region, the total current is proportional to the average vibration velocity in the packet (equation (1)), which is zero due to the absence of a DC component. When the wave packet passes an interface of different conductivities, the portion inside the high a region contributes more current with the same velocity: thus the integral in equation (1) is no longer zero. When the wave packet passes an interface of different mass densities but no change in conductivity, the portion in the low density region have higher vibration velocities, therefore the integral in equation (1) is also non-zero. In both cases the total Hall effect current becomes non-zero, and the resulting Hall voltage marks the presence of the interface.

Figure 1C:
FIG. 1C shows the σ/ρ gradient along the Z axis corresponding to FIG. 1B, in accordance with an illustration of principles of the present invention.
Figure 1D:
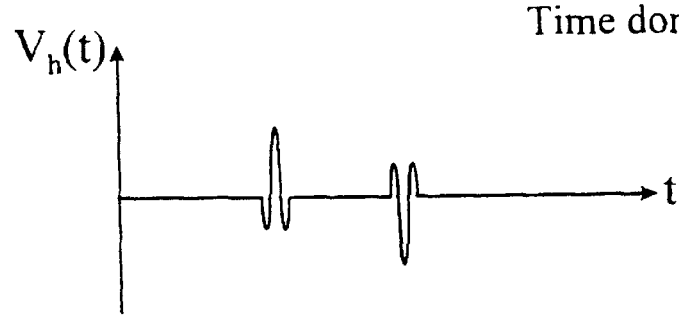
FIG. 1D shows the Hall voltage acquired over time as the ultrasound wave packet of FIG. 1A propagates through the sample having the conductivity σ to mass density ρ spatial distribution of FIG. 1B, in accordance with an illustration of principles of the present invention.

By way of illustration, in applying equation (7) to the example shown in FIGS. 1A–B, the gradient of $\sigma/\rho$ is non-zero only at the interfaces $z_1$ and $z_2$ (FIG. 1C). The ultrasound momentum $M(z,t)$ is carried by the wave packet as it travels along the Z axis. The Hall voltage $V_h$, is a convolution of the ultrasound momentum $M(z,t)$ with the $\sigma/\rho$ gradient (equation (7)). When the packet passes the two interfaces successively, the integrand in equation (7) two interfaces successively, the integrand in equation (7) becomes non-zero, giving rise to a Hall voltage. Thus the time course of the Hall voltage contains two peaks representing the two interfaces (FIG. 1D). The time of each peak marks the position of its corresponding interface. The polarity of the two peaks are opposite, because the $\sigma/\rho$ gradient at $z_1$ and $z_2$ are in opposite directions. In this fashion HEI converts spatial information into the time domain much like conventional echo ultrasound. Many methods used in echo ultrasound to collect 2 or 3-dimensional images, such as line scan and phased array detection, also apply to HEI. Similarly, motion measurements based on Doppler effect in echo ultrasound can be readily implemented in HEI.

Figure 2:
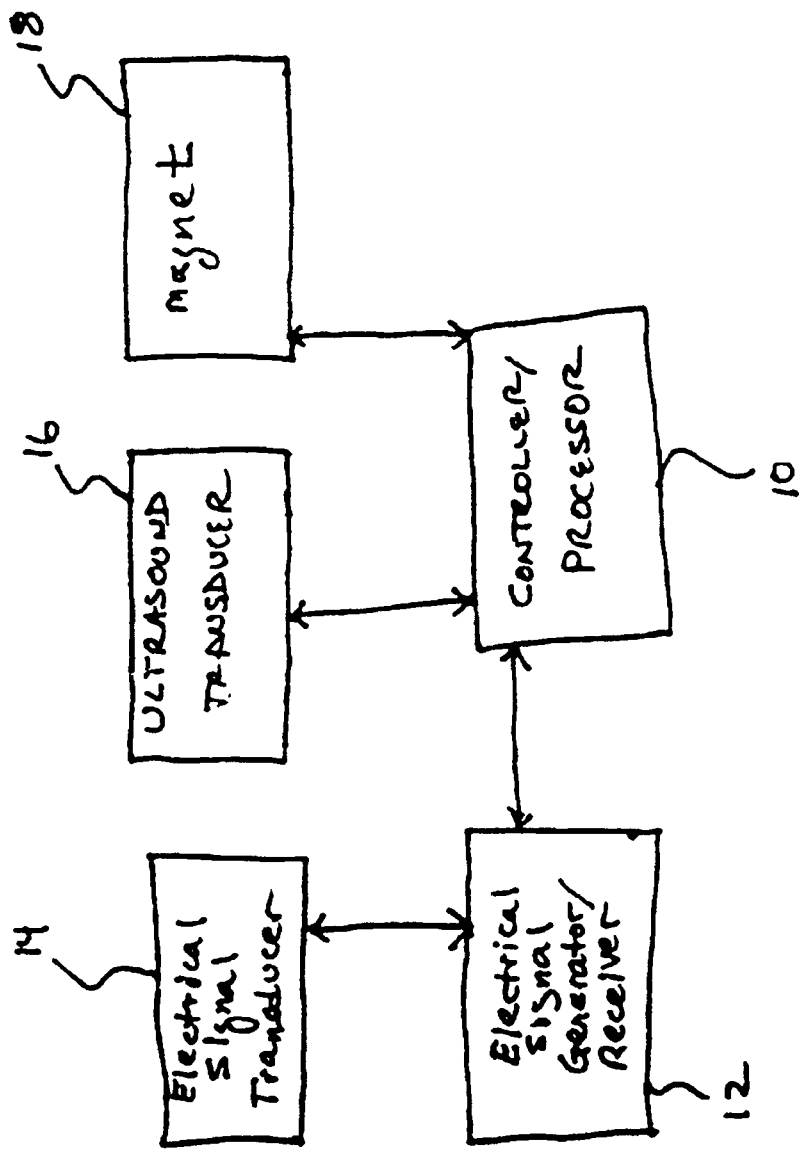
FIG. 2 is a block diagram of an ultrasound-Hall imaging system in accordance with practicing the present invention.

Referring now to FIG. 2, there is shown a functional block diagram of a system for practicing the various embodiments of the present invention. The system includes a magnet 18 for generating a large static magnetic field, an ultrasound transducer 16, and electrical signal transducer 14, an electrical signal generator/receiver 12, and a controller/processor 10. A subject (e.g. human body) or object (not shown) is positioned in the system such that the static magnetic field traverses the subject/object.

Based on the Lorentz forces upon which the Hall effect (HE) is based, the electrical signal transducer 14, ultrasound transducer 16, and magnetic field generated by magnet 18, are oriented such that they have mutually orthogonal components for detecting/generating the signals of interest, and preferably, they are established in an orthogonal relationship.

Electrical signal transducer 14 may include one or more (e.g. an array) coils for inductive coupling of electrical signals with the object or body, or alternatively may include one or more electrodes for direct contact to the object or subject for direct conduction of electrical signals with the object or subject.

In an embodiment of the invention wherein ultrasound pulses are coupled into object or body and electrical signals are detected, electrical signal transducer 14 receives these electrical signals (either inductively or conductively) and electrical signal generator/receiver 14 acts as a receiver (e.g., radiofrequency detector). Alternatively, in an embodiment of the invention wherein ultrasound pulses are detected from the object or body and electrical signals are coupled into the object or body, then electrical signal transducer 14 transmits (inductively or conductively) the electrical signal (e.g., pulse) generated by electrical signal generator 12 (e.g., RF generator) to the object or body.

Similarly, ultrasound transducer 16 is appropriately employed to either generate or detect ultrasound signals (e.g., pulses), depending on the implementation. Ultrasound transducer 16 may be, for example, a conventional linear array probe which scans a sector in a plane by steering the direction of the ultrasonic beam transmitted by ultrasonic transducer 16 according to phase array principles. Alternatively, for the second implementation for example, ultrasound transducer 16 may be either a one-dimensional or a two-dimensional array in which each element of the array concurrently detects ultrasound energy from the object or body, and through data processing techniques (e.g., Fourier transform) operating on the signals from all the elements, either a two-dimensional image or three-dimensional image, respectively, is reconstructed.

Moreover, with regard to transducers, fiber optic ultrasonic sensors and photoacoustic transducers may be the basis for high sensitivity sensors and efficient transmitters which are not affected by the magnetic field, and are immune to any electromagnetic interference. J. A. Bucaro, J. H. Cole, A. D. Dandridge, T. G. Giallorenzi and N. Lagakos. "Fiber optic acoustic sensors," in *Optical testing and metrology*. Bellingham, Wa. Society of Photo-Optical Instrumentation Engineers, 1986. pp. 182; Q. X. Chen, R. J. Dewhurst, P. A. Payne and B. Wood, "A new laser-ultrasound transducer for medical applications." *Ultrasonics* vol. 32, pp. 309–313, 1994; S. Knudsen, A. M. Yurek, A. B. Tveten and A. D. Dandridge, "High-sensitivity fiber optic planar ultrasonic microphone," in *Proceedings of the International Society for Optical Engineering*. vol. 2360. pp. 396. 1994; J. F. Dorighi. S. Krishnaswamy and J. D. Achenbach, "Embedded fiber optic ultrasonic sensors and generators." in *Proceedings of the International Society for Optical Engineering*, vol. 2574. pp. 46, 1995.

The controller/processor 10, which may be a conventional computer, workstation, or adapted ultrasound processing system, is coupled to electrical signal generator/receiver 12, ultrasound transducer 16, and magnet 18, for controlling the overall signal acquisition sequences and preferably, also for processing and displaying images according to these acquisitions.

In a first implementation, an ultrasound pulse is propagated into the body by ultrasound transducer 16. In the presence of a static magnetic field provided by magnet 18, the Lorentz force associated with the local displacement of conductive moieties in the body as the ultrasonic pulse propagates through the body results in the generation of an electrical signal. The electrical signal is detected with electrical signal transducer 14 and electrical signal receiver 12 as the ultrasonic pulse propagates through the body. Controller/processor 10 acquires the electrical signal and processes this information to produce an image (e.g., two-dimensional or three-dimensional) which is weighted by conductivity (which includes any function of the conductivity). For instance, the image contrast (e.g., intensity, gray-scale, and/or color) may be weighted by the conductivity gradient magnitude, the conductivity gradient magnitude and polarity, the relative conductivity (e.g., the integral of the conductivity gradient), etc. It may be understood that the ultrasound pulse may be focussed and scanned to provide spatial localization for imaging.

In accordance with the above descriptions, in the presence of a static magnetic field, an ultrasonic pulse propagating in the tissues exhibits the Hall effect (HE) due to the conductivity of the tissues. Hall effect is the phenomenon that when a conductive object (such as a saline solution) moves in a static magnetic field, a voltage develops in the direction perpendicular to both the magnetic field and the direction of movement. The amplitude of the voltage is proportional to the product of the conductivity of the object, the speed of movement, and the magnetic field strength (i.e., $V \alpha \sigma vB$; $\sigma$ being the conductivity of the object, v being the speed of movement, and B the strength of the magnetic field). With the ultrasonic pulse, Hall voltages arise from the vibrational movements, and can be detected with various electrical circuits. These signals represent the progression of the ultrasonic pulse in the body, and therefore information of the tissue—tissue interfaces it encounters. The signal amplitude and phase are related to the conductivities of the tissues and the acoustic vibration amplitude and phase of the pulse. The Hall effect signals therefore can be used to reconstruct an image of the volume in which the sonic pulse propagates.

It may be understood, therefore, that the imaging method according to this first implementation of the present invention is similar to current ultrasonic imaging in that ultrasonic pulses are used to interrogate the body. A fundamental difference, however, is the method to monitor the progression of the pulse. In current (i.e., conventional) ultrasonic imaging since the progression of the pulse is monitored by detecting the echoes of the pulse reflected back at the tissue—tissue interfaces, it is entirely a characterization of the acoustic impedances of the tissues. The acoustic path involved starts from the transducer that generates the ultrasonic pulse, reaches the tissue—tissue interfaces, and back to the transducer if it is also used to receive the echoes, or to another receiving transducer.

In the ultrasound-Hall effect method, the progression of the ultrasonic pulse is monitored by detecting the Hall effect signals it induces with electrical circuits. The Hall effect voltages reach the electrical circuits almost instantaneously (at the speed of light); therefore, the progression of the ultrasonic pulse is instantaneous and constantly monitored. Because the Hall effect signal is directly related to the electrical conductivities of the tissues, it characterizes the conductivities and the acoustic impedances. The Hall effect method thus has a different contrast mechanism from the current (conventional) ultrasound imaging method. Because of the instantaneous nature, the acoustic path involved in seeing an interface is from the transducer that generates the pulse to the interface, usually half of that of the current method. The signal attenuation along the acoustic path is reduced.

As described above, ultrasound-Hall effect according to the present invention, may also be performed in the exact reciprocal fashion of the above first implementation. In this second implementation, a pulsed current distribution at the ultrasonic frequency is set up in the body via electrical signal generator 12 and electrical signal transducer 14. In the presence of a static magnetic field provided by magnet 18, the Lorentz force on the pulsed current results in an ultrasonic pulse distribution in the body. The ultrasonic pulse is detected with ultrasonic transducer 16 as it propagates through the body to the location of the transducer. Controller/processor 10 acquires the ultrasonic pulse signals and processes this information to produce an image (e.g., two-dimensional or three-dimensional). As described above regarding the electrical circuit used to detect the Hall voltages, the electrical circuit used in the reciprocal case to generate the pulsed current distribution can generally be of two types. Electrodes can be in direct contact with the body (direct electric coupling), or the circuit can inductively couple with the body (magnetic inductive coupling).

The reciprocity relation of linear electrodynamic systems, derived from Onsager's relations, warrants that the signal obtained from the above two realizations or embodiments are identical. Their sensitivity and spatial resolution, however, will be determined by two different sets of parameters.

Figure 3A:
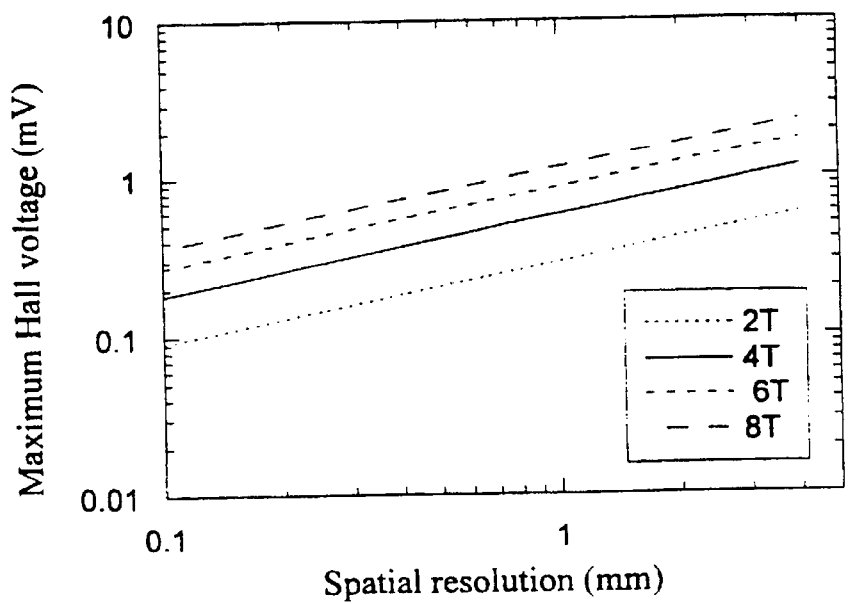
FIG. 3A depicts estimated maximum Hall voltage signal vs. spatial resolution from a fat-muscle interface in the voltage detection mode of HEI, for different magnetic field strengths, in accordance with an embodiment of the present invention.

In the Hall voltage detection method, a limiting factor is the ultrasound pulse intensity which in biological structures must not exceed the cavitation threshold. The cavitation threshold for soft tissue has been established empirically as the ratio (peak pressure)$^2$/(ultrasound frequency)~0.5 (MPa$^2$/MHz). R. E. Apfel and C. K. Holland, "Gauging the likelihood of cavitation from short-pulse, low-duty cycle diagnostic ultrasound,", *Ultrasound Med. Biol.* vol. 17, pp. 179–185, 1991; L. A. Crum. R. A. Roy, M. A. Dinno. C. C. Church, R. E. Apfel, C. K. Holland and S I. Madanshetty, "Acoustic cavitation produced by microsecond pulses of ultrasound: A discussion of some related results, "*J. Acoust. Soc. Am.* vol. 91, pp. 1113–1119, February 1992. Based on this index an estimate of the maximum Hall voltage from a muscle-fat interface can be made for the line scan method. Using equation (7), assuming that the width of the ultrasound beam W=1 cm, the current collection factor 100%, $R_d$=50 Ω, the maximum Hall voltage for a range of field strength and spatial resolution is estimated as shown in FIG. 3A. This voltage is on the order of 1 mV. In practice, the signal level is generally lower because the ultrasound pressure is below the cavitation threshold, the detection electrodes are usually remote from the scanned region, and the ultrasound beam may not be perpendicular to the magnetic field (e.g., see polystyrene example hereinbelow). Signal averaging over multiple acquisitions may be used to improve the signal-to-noise ratio. In biomedical imaging such averaging is evidently practicable and applicable when acquiring 1-dimensional profiles or 2-dimensional images with phased array detection, since each scan is on the order of 200 μS or less, and the required frame rate is often less than 50 frames/sec (20 ms/frame). Physiological motions such as heartbeat and blood flow induce Hall voltages in the DC~100 Hz range, therefore they do not contribute to the noise in HEI (MHz).

Figure 3B:
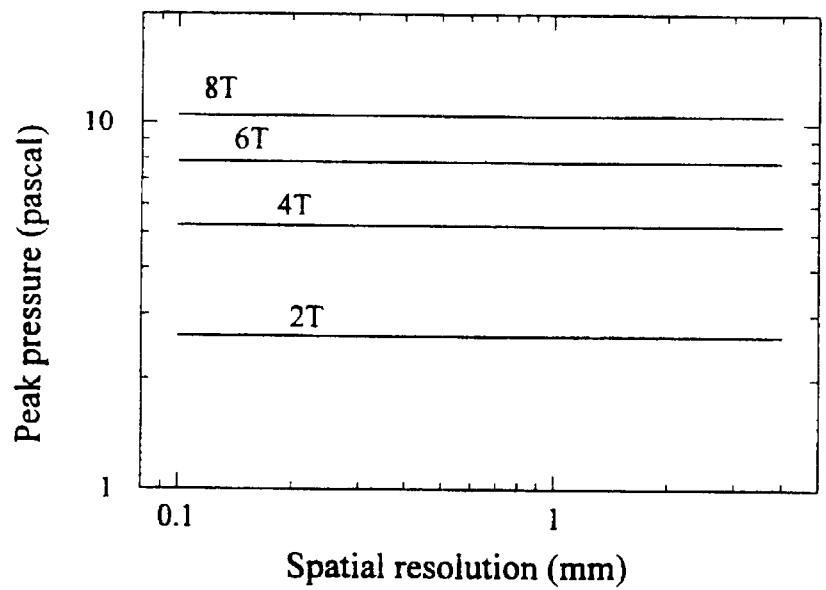
FIG. 3B depicts estimated maximum ultrasound pressure signal vs. spatial resolution from a fat-muscle interface in the ultrasound detection mode, for different magnetic field strengths, in accordance with an embodiment of the present invention.

In the ultrasound detection mode of HEI, the limit on sensitivity is the maximum current allowed in the object. In biological tissue the threshold is set by nerve stimulation. The duration of the electrical impulse determines the length of the ultrasound pulse it produces, and therefore the spatial resolution of the image. To achieve millimeter or higher resolution, the pulse duration must be on the order of a microsecond, or one hundredth the strength-duration time constant of human sensory and muscular nerves. J. P. Reilly. *Electrical Stimulation and Electropathology.* New York. Cambridge University Press, 1992, ch. 7, pp. 238. In this short time limit the nerve stimulation threshold is established as the product (electric field)×(pulse duration)~$2 \times 10^{-3}$ Vs/m. J. P. Reilly, ibid., ch. 4, p. 119. Based on this index, the peak pressure of the ultrasound signal from a fat-muscle interface can be estimated for a range of $B_0$ and spatial resolution. In the millimeter resolution range the peak pressure was found to be on the order of 5 pascal, and dependent only on $B_0$ (FIG. 3B). Again, this value is compromised in practice because the electrical impulses are usually below the nerve stimulation level, the electric field is not perpendicular to $B_0$, and the ultrasound sensors are often remote from the region of interest.

It may be appreciated therefore that the conductivity contrast mechanism of the imaging method according to the present invention provides a new imaging modality. This parameter of the tissues, which heretofore has not been readily obtained in vivo, may contain diagnostic information of certain pathologies, such as diseases in kidneys, where the electrolyte concentration is an indicative index.

More specifically, in biomedical imaging ultrasound has been very effective, although it has inherent difficulties in differentiating soft tissue, since muscle, fat and blood differ in their acoustic impedances by less than 10%. S. A. Goss. R. L. Johnston and F. Dunn, "Comprehensive compilation of empirical ultrasound properties of mammalian tissues." *J. Acoust. Soc. Am.* vol. 64, 1978, pp. 423–457. In comparison, the conductivities of soft tissue at ultrasound frequencies range over a factor of four, (K. R. Foster and H. P. Schwan, in *CRC Handbook of Biological Effects of Electromagnetic Fields*, edited by C. Polk and E. Postow, Boca Raton, Fla., CRC Press Inc., 1986, Part I), while their mass densities are very similar. This enables HEI to differentiate soft tissue based mainly on conductivity differences. The acoustic path length in HEI is also half that of ultrasound, greatly reducing the acoustic attenuation and dispersion. These characteristics of HEI may potentially improve the penetration depth, tissue contrast and characterization in an ultrasound exam.

With regard to new diagnostic information the electrical constants of tissue reflect their physiological state, such as water content and adiposity. K. R. Foster and H. P. Schwan, in *CRC Handbook of Biological Effects of Electromagnetic Fields*, edited by C. Polk and E. Postow, Boca Raton, Fla., CRC Press Inc., 1986, Part I; E. C. Burdette, F. L. Cain and J. Seals, in *Medical Applications of Microwave Imaging.* edited by L. E. Larsen and J. H. Jacobi. New York, IEEE Press, 1986, pp. 23. It has been shown that tumors and especially necrotic regions have up to 10 times higher conductivity than normal tissue, (K. R. Foster and H. P. Schwan. ibid. Part I, pp. 68), providing a good contrast mechanism in HEI. With its sensitivity to fat, the HEI method according to the present invention implemented with small intravascular probes could be used to characterize atherosclerotic plaques, which is difficult with existing imaging methods.

It may further be appreciated that with the development of ultrasound array sensors, HEI may be used for mammography or imaging of skin and subcutaneous structures, where it is relatively easy to arrange the magnet, the electrodes and the ultrasound sensors, and the entire device can be relatively compact.

It is noted that while HEI according to the present invention has myriad biological and medical applications, it is also well suited for many other applications. For instance, HEI may also have a role in material sciences and microelectronics, where it could be used to study the conductivity and dielectric properties at very high frequencies in structures susceptible to ultrasound. Similarly, it may also be used for manufacturing quality control and reliability testing.

It may also be appreciated that with the magnetic inductive coupling scheme discussed hereinabove, multiple sensing coils forming an array in space can be used to detect the Hall signal. This provides flexibility regarding spatial sensitivity. Even more attractive is the option that given enough signal-to-noise, which is directly proportional to the magnetic field strength, the signals from the multiple sensing coils can be used to reconstruct an image of the ultrasound wave front, thus overcoming the inherent problem of beam expansion and low angular resolution away from the origin of the beam in the conventional ultrasound imaging method. Such a wavefront reconstruction technique provides for one-shot 3D imaging, giving ultra-fast-temporal resolution. Currently multiple ultrasound transducers are occasionally used to approach this, but hindered by the limited sizes of the acoustic windows in the body. The magnetic inductive coupling is not limited because r.f. magnetic fields penetrate the body with negligible perturbation. At a field strength of 4 Tesla (i.e., 4 T), the achievable S/N ratio may limit the number of array coils to a few, similar to the array coil receive situation in MRI. However since the ultrasound-Hall imaging scheme requires strong field strength only in the volume of interest, no requirement on the uniformity of the field, and minimal requirement on the stability of the field, much higher field strengths are practicable.

The following examples are presented to illustrate features and characteristics of the present invention, which is not to be construed as being limited thereto.

EXAMPLE 1

In this example, ultrasound-Hall effect imaging is demonstrated in a simple one-dimensional imaging experiment, in accordance with the first embodiment of the present invention described hereinabove.

Figure 4A:
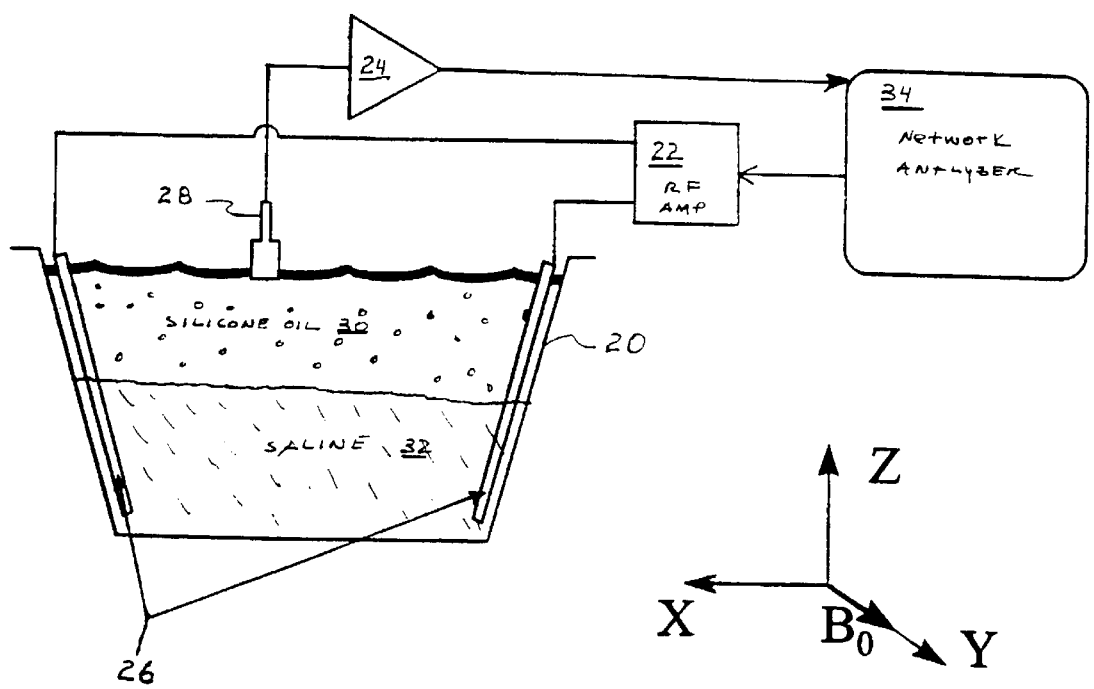
FIG. 4A schematically illustrates an experimental setup for a simple one-dimensional imaging experiment demonstrating a principle for an embodiment of the present invention.

The experimental setting used is shown in FIG. 4A. As stated, the reciprocal method was used. The plastic beaker 20 contained two layers of liquids, the top layer was silicone oil 30, the bottom layer was 0.3% NaCl solution 32 (diluted irrigation saline solution). A pulsed current distribution of 1 MHz bandwidth and 2.1 MHz center frequency was generated in the beaker with the r.f. amplifier 22 in response to an input stimulus from network analyzer 34, and coupled into the beaker 20 via electrodes 26, which had textured surfaces to reduce coherent speculating echoes from the vibration of the electrodes. The induced ultrasonic pulse was detected with the ultrasound transducer 28 and amplified with a low noise amplifier 24 and provided to the receive port of network analyzer 34.

Figure 4B:
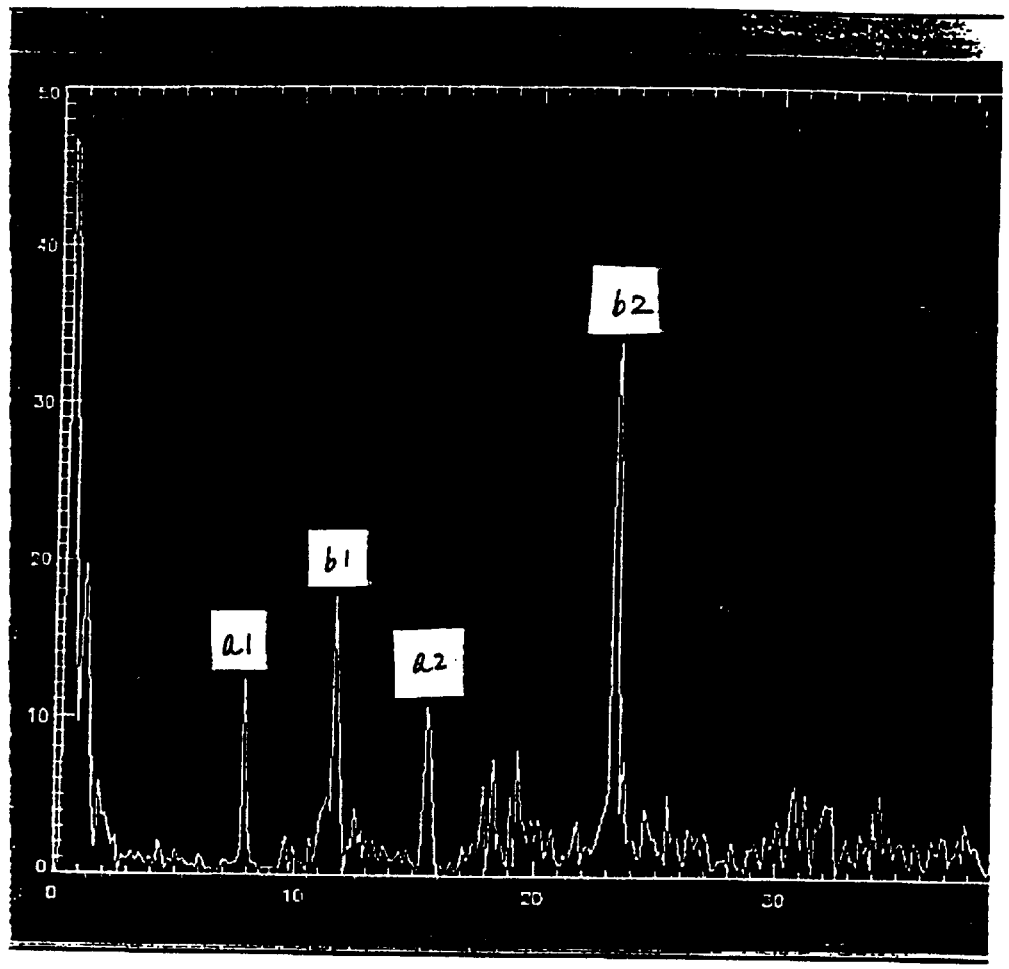
FIG. 4B shows the experimentally measured results of the signal acquired by the ultrasound probe for the setup of FIG. 4A, in accordance with the present invention.
Figure 4C:
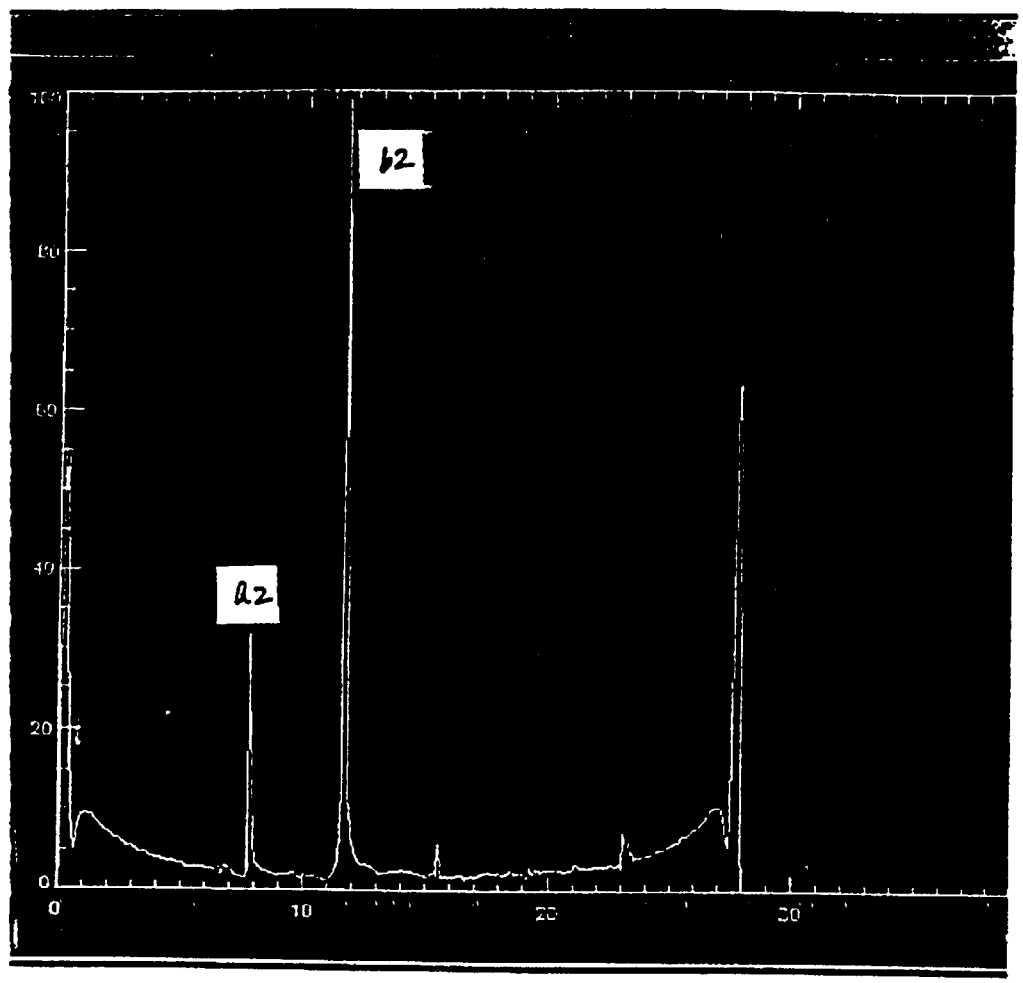
FIG. 4C shows the experimentally measured results of an ultrasound signal acquired for the setup of FIG. 4A using conventional ultrasound techniques.

FIG. 4B shows the received signal, plotted as a function of distance in centimeters. Peak a1 and b1 correspond to the oil-saline interface and the saline-beaker interface, respectively, which are independently measured with the conventional ultrasound method, shown in FIG. 4C. Peak a2 and b2 correspond to the conventional ultrasound echoes through direct electromagnetic coupling between the transducer and the electrical circuit.

Figure 4D:
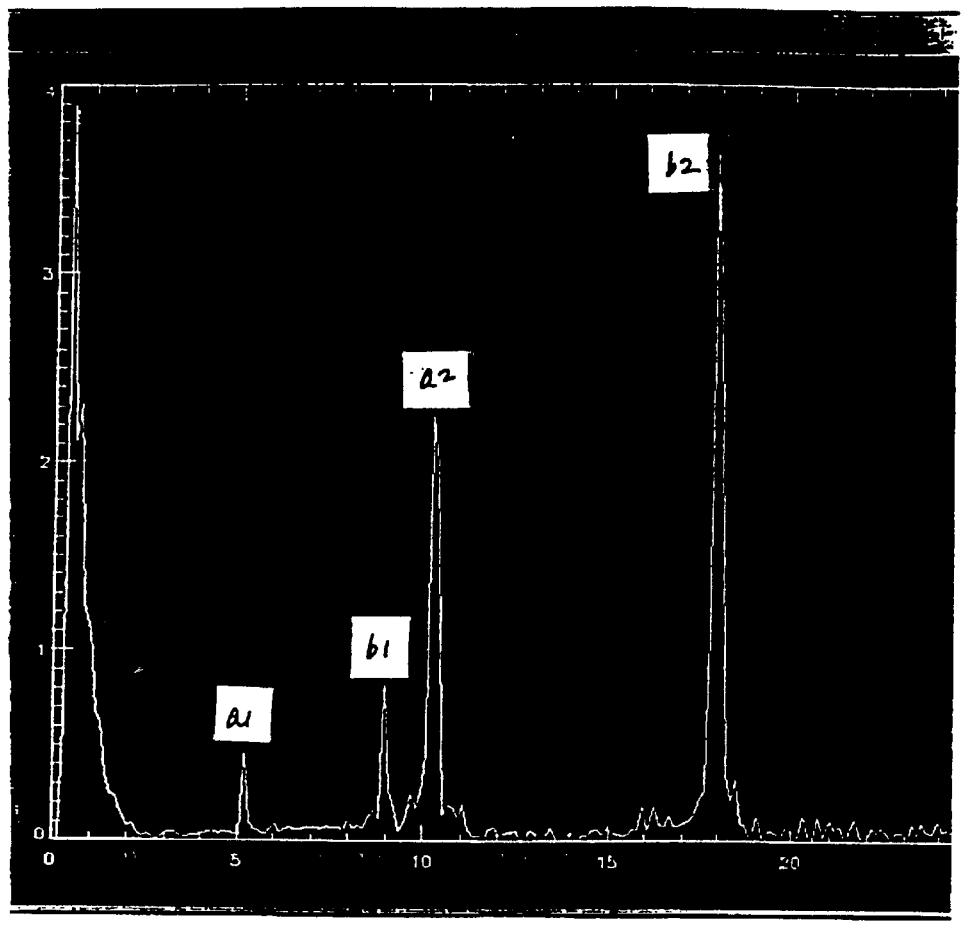
FIG. 4D shows the experimentally measured results of the signal acquired by the ultrasound probe for the setup of FIG. 4A, with the beaker placed at the center of the magnet, in accordance with the present invention.
Figure 4E:
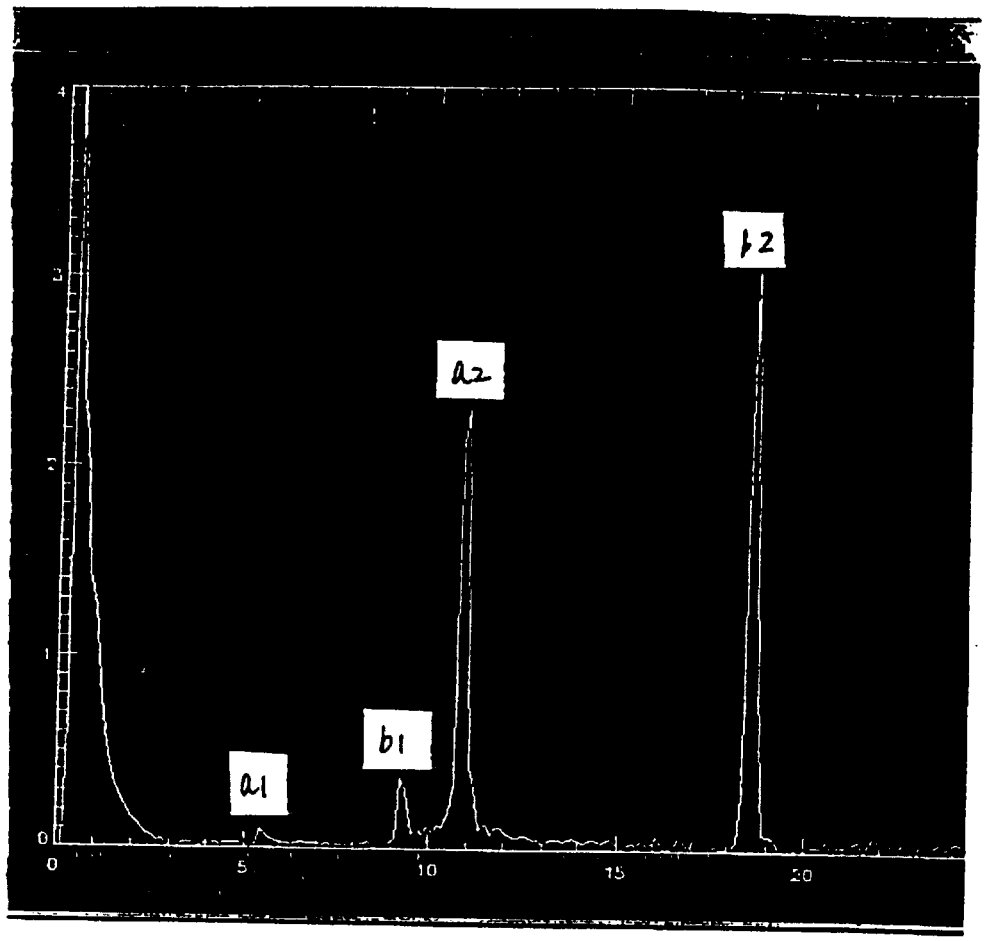
FIG. 4E shows the experimentally measured results of the signal acquired by the ultrasound probe for the setup of FIG. 4A, with the beaker placed near the edge of the magnet, in accordance with the present invention.

FIG. 4D and FIG. 4E show a similar experiment with the beaker placed at the center of the magnet and the edge magnet, respectively. Because the magnetic field strength is decreased from the center to the edge, the Hall peaks a1 and b1 decreased. The amplitudes of the conventional ultrasound echoes a2 and b2 stayed relatively constant.

The achievable signal level may be estimated from the one-dimensional experiment described above. The signal level of the Hall peaks were approximately 2.5 $\mu$V, given an excitation peak voltage of 15 volts. If 300 volts excitation is used, which is the typical operating voltage for current pulsed ultrasound imaging, 50$\mu$V peak signal can be reached. Assuming a 500 KHz acquisition bandwidth and 50 ohm output impedance, the thermal noise at room temperature is 0.65$\mu$V. Accordingly, based on the simple one-dimensional experiment, the ideal achievable signal-to-noise ratio is 70:1. Given all the practical factors, the realizable S/N is probably on the order of 30:1. The coherent speckles in current imaging methods cause the signal-to-noise ratio to be much lower than this value, thus the intrinsic signal-to-noise ratio may not after all constitute a limitation.

EXAMPLE 2

In this second example, ultrasound-Hall effect imaging is demonstrated in a simple two-dimensional imaging experiment, in accordance with the second embodiment of the present invention described hereinabove.

Figure 5A:
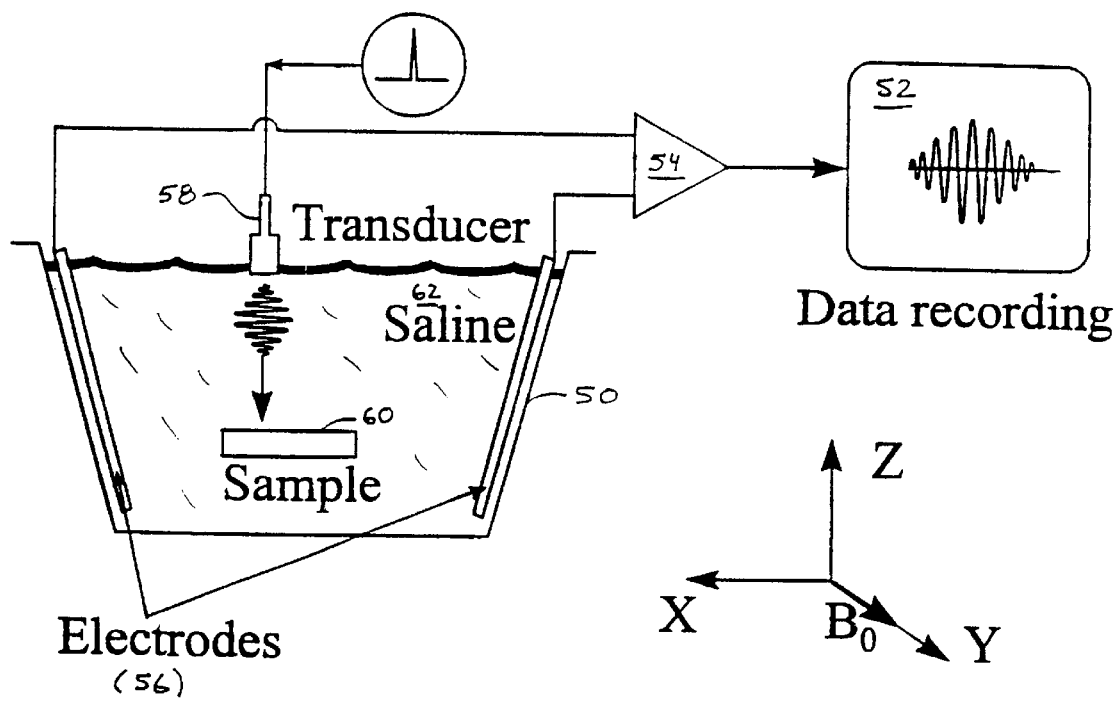
FIG. 5A is a diagram of an experimental setup for HEI of a sample, in accordance with an embodiment of the present invention.

More particularly, to demonstrate the feasibility of HEI, a simple device, essentially similar to that used in example 1 hereinabove, was constructed to form cross-sectional images of objects (samples) 60 suspended in a plastic chamber 50 of saline solution 62 (e.g., 0.4% NaCl solution) placed in a 4 T magnet providing magnetic field $B_0$. (FIG. 5A). The dimensions of the chamber 50 were 27 cm (xdimension)×17 cm (Y)×22 cm (Z). The electrodes 56 were two exposed copper wire segments. The piezoelectric ultrasound transducer 58 used had a center frequency of 1 Hz, and a 6 dB bandwidth of 0.6 MHz. An electrical pulser input single-phase electrical pulses of approximately 0.5$\mu$s duration into the transducer 58, which in turn emitted ultrasound pressure pulses into the chamber. The detected Hall voltage was amplified (low noise amplifier 54) by 60 dB gain, filtered by a 0.1 MHz~3 MHz bandpass filter, and digitized at 5 megasample/sec for data storage (recording) 52.

Figure 5B:
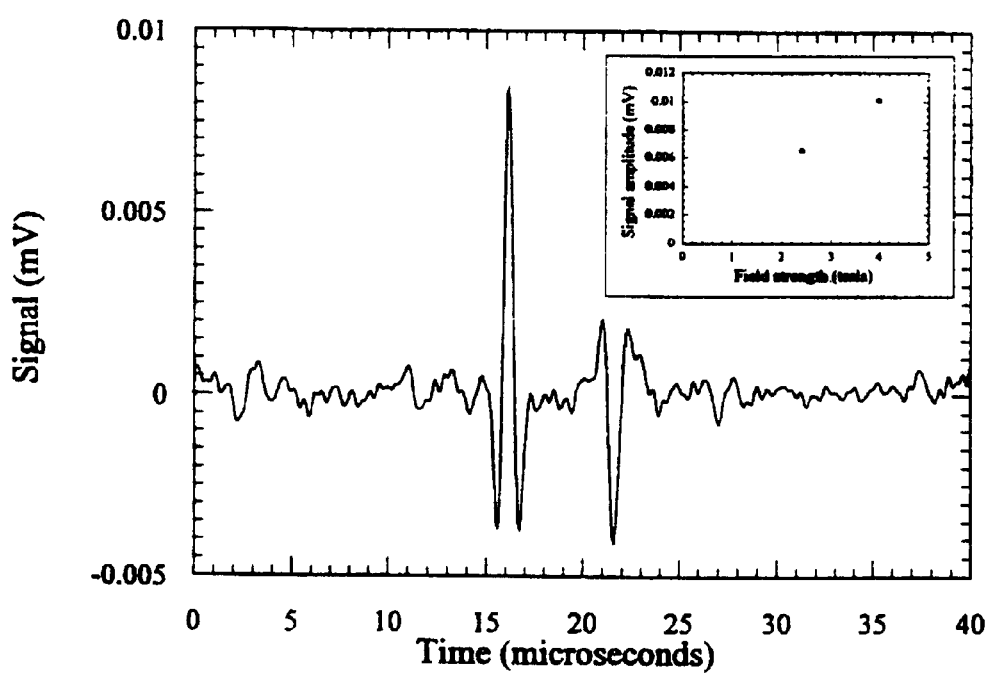
FIG. 5B shows an Hall voltage time trace collected for a rectangular polystyrene block immersed in saline using the experimental setup of FIG. 5A, and also includes an inset showing the acquired Hall voltage magnitude dependence on the applied magnetic field strength, in accordance with an embodiment of the present invention.

In a first two-dimensional imaging trial, a rectangular polystyrene block was immersed in the saline. The magnetic field $B_0$, was in the "Y" direction. A piezoelectric transducer emitted longitudinal ultrasound waves with both the wave vector and the physical vibration in the "Z" direction. The Lorentz force from the vibration was in the "X" direction, and the resulting Hall voltage was detected with electrodes placed in the chamber. Immediately after the onset of the ultrasound pulse, the Hall voltage was recorded for up to 100 $\mu$s, the time required for the ultrasound wave packet to traverse the chamber. FIG. 5B shows such a Hall voltage time trace collected for the rectangular polystyrene block immersed in saline. The two peaks in the time trace represent the upper and lower surfaces of the polystyrene block. The amplitude of the second peak is lower than the first peak due to attenuation and acoustic reflection at the upper surface. As described in equation (7), the opposite polarity of the peaks resulted from the opposite $\sigma/\rho$ gradient at the two interfaces. Also according to equation (7), the Hall voltage is proportional to the magnetic field strength. This was experimentally demonstrated as indicated by the inset of FIG. 5B, where the signal amplitude measured at 2.4 T and 4 T are plotted versus field strength. It is noted that in this polystyrene block experiment (axial resolution 2 mm, beam width approximately 2.5 cm) the measured Hall voltage was about 0.1% of its theoretical maximum because the ultrasound pulse was only one tenth the cavitation threshold and the electrodes were relatively far from the sample.

Figure 5C:
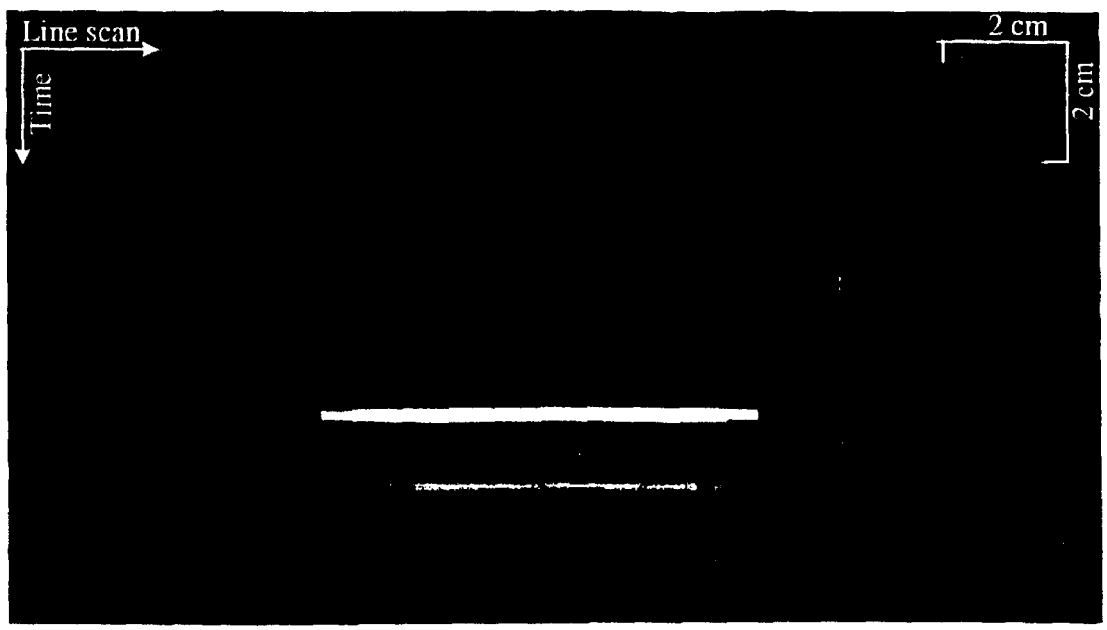
FIG. 5C is an HE image generated from magnitude reconstruction of signals acquired using the experimental setup of FIG. 5A for a polystyrene block immersed in saline, in accordance with the present invention.

A 2-dimensional image was formed with the line scan method by moving the transducer in 0.5 cm increments across the chamber, while recording the time course of the Hall voltage at each position. These traces were displayed side by side in grey scale after a magnitude calculation, to form a 2-dimensional image. FIG. 5C shows such an image of the polystyrene block, with the time axis in the vertical direction and the horizontal axis scanned by moving the ultrasound transducer as described. The interfaces between the block and the saline solution are readily observed. Polarity images, where the magnitude and polarity (i.e., positive or negative) of the acquired signals in each pixel are represented according to a color spectrum were also generated (not shown).

In a second two-dimensional imaging trial, bacon was chosen as an example of a biological structure since it has layers of high (muscle) and low (fat) conductivity soft tissue. The HE image of a block of bacon suspended in the chamber is shown in FIG. 5D, along with a photograph and an echo ultrasound image generated using the same transducer and line scan procedure. HEI depicts the soft tissue interfaces between the fat and muscle layers better (i.e., better differentiates between fat and muscle) than echo ultrasound because of the significant changes in conductivity between the layers, to which HEI is sensitive and conventional echo ultrasound is not sensitive.

Although the above description provides many specificities, these enabling details should not be construed as limiting the scope of the invention, and it will be readily understood by those persons skilled in the art that the present invention is susceptible to many modifications, adaptations, and equivalent implementations without departing from this scope and without diminishing its attendant advantages. It is therefore intended that the present invention is not limited to the disclosed embodiments but should be defined in accordance with the claims which follow.

I claim:

1. A method for acquiring information on the conductivity distribution in an object, said method comprising the steps of:

applying a magnetic field to said object;

applying an excitation signal along a direction non-parallel to said magnetic field and which induces a local charge displacement in said object as said excitation signal propagates in said object, said local charge displacement capable of being induced in the bulk of said object; and acquiring a signal encoded with information indicative of local conductivity of said object for regions along path traversed by said excitation signal, said signal related to an interaction between said magnetic field and said local charge displacement as said excitation signal propagates in said object, said regions capable of being located in the bulk of said object.

2. The method according to claim 1, further comprising the step of generating an image from said signal, said image weighted by a function of conductivity of said object, said image thereby representing the conductivity distribution of said object.

3. The method according to claim 2, wherein said image is weighted by conductivity gradient magnitude.

4. The method according to claim 2, wherein said image is weighted by conductivity gradient magnitude and polarity.

5. The method according to claim 2, wherein said image is weighted by conductivity magnitude.

6. The method according to claim 1, wherein said excitation signal is an acoustic signal which propagates through said object, and said signal is an electrical signal corresponding to a Lorentz interaction between said magnetic field and local displacement of said object as said acoustic signal propagates through said object.

7. The method according to claim 6, wherein said acoustic signal is localized along a direction of propagation into said object, and wherein multiple acoustic signals are directed along respective propagation directions into said object, thereby spatially scanning said object with the multiple acoustic signals.

8. The method according to claim 6, wherein said electrical signal is acquired by at least one coil inductively coupled to the object.

9. The method according to claim 6, wherein said electrical signal is acquired by at least one electrode directly coupled to said object.

10. The method according to claim 1, wherein said excitation signal is an electrical signal, and said signal is an acoustic signal corresponding to a Lorentz interaction between said magnetic field and local electrical current in said object as said electrical signal propagates through said object.

11. The method according to claim 10, wherein said acoustic signal is detected along a given direction, and wherein said given direction is scanned.

12. The method according to claim 10, wherein said acoustic signal is detected with a transducer which includes an array of elements that concurrently detect acoustic energy respectively localized along respective directions.

13. The method according to claim 1, wherein said object is at least a portion of a human body.

14. A system for acquiring information on the conductivity distribution in an object, said system comprising:
   a magnet which applies a magnetic field to said object;
   means for generating an excitation signal applied along a direction non-parallel to said magnetic field and which induces a local charge displacement in said object as said excitation signal propagates in said object, said local charge displacement capable of being induced in the bulk of said object; and
   means for acquiring a signal encoded with information indicative of local conductivity of said object for regions along path traversed by said excitation signal, said signal related to a Lorentz interaction between said magnetic field and said local charge displacement as said excitation signal propagates in said object, said regions capable of being located in the bulk of said object.

15. The system according to claim 14, further comprising means for generating an image from said signal, said image weighted by a function of conductivity of said object, said image thereby representing the conductivity distribution of said object.

16. The system according to claim 14, wherein said excitation signal is an acoustic signal which propagates through said object, and said signal is an electrical signal corresponding to a Lorentz interaction between said magnetic field and local displacement of said object as said acoustic signal propagates through said object.

17. The system according to claim 14, wherein said excitation signal is an electrical signal, and said signal is an acoustic signal corresponding to a Lorentz interaction between said magnetic field and local electrical current in said object as said electrical signal propagates through said object.

18. An apparatus for acquiring information on the conductivity distribution in an object, comprising:
   an acoustic transducer coupled to said object and which generates an incident acoustic signal that propagates into the bulk of said object;
   a magnetic element that generates a magnetic field in said object;
   an electrical signal receiver that receives an electrical signal related to an interaction between said acoustic signal and said magnetic field as said acoustic signal propagates through the bulk of said object.

19. The apparatus according to claim 18, further comprising a processor that generates an image of said object based on said electrical signal.

20. The apparatus according to claim 18, wherein said electrical signal receiver includes at least one coil inductively coupled to the object.

21. The apparatus according to claim 18, wherein said electrical signal receiver includes at least one electrode directly coupled to said object.

22. The apparatus according to claim 18, wherein said acoustic transducer generates said acoustic signal as a beam localized along a direction of propagation into said object, and wherein said acoustic transducer generates a series of acoustic signals each directed along a respective propagation direction into said object, thereby spatially scanning said object with the series of acoustic signals.

23. An apparatus for acquiring information on the conductivity distribution in an object, comprising:
   a magnetic element that generates a magnetic field in said object;
   an electrical signal source that generates a time-varying electrical signal which is applied along a direction non-parallel to said magnetic field and which propagates through the bulk of said object; and
   an acoustic transducer coupled to said object and which detects an acoustic signal that propagates through the bulk of said object and relates to an interaction between said time-varying electrical signal and said magnetic field.

24. The apparatus according to claim 23, wherein said acoustic transducer detects acoustic energy localized along a given direction, and wherein said given direction is scanned.

25. The apparatus according to claim 23, wherein said acoustic transducer includes an array of elements that concurrently detect acoustic energy from the object.

26. A method for imaging the conductivity distribution in an object, said method comprising the steps of:
   applying an electrical excitation signal and a magnetic field to said object, the electrical excitation signal being along a direction non-parallel to said magnetic field, to induce a local charge displacement in said object as said excitation signal propagates in said object;
   acquiring an acoustic signal using a transducer that includes an array of elements that concurrently detect said acoustic signal, said acoustic signal encoded with information indicative of local conductivity of said object for regions along path traversed by said excitation signal, said acoustic signal corresponding to a Lorentz interaction between said magnetic field and said local charge displacement as said excitation signal propagates in said object; and generating an image from said acoustic signal, said image weighted by a function of conductivity of said object, said image thereby representing the conductivity distribution of said object.

27. A method for imaging an object, comprising the steps of:

applying an electrical excitation to said object in the presence of a magnetic field to cause Hall effect induction of an ultrasonic signal distributed in the bulk of said object;

acquiring the induced distributed ultrasonic signal using an array of ultrasound transducer elements that concurrently detect the induced distributed ultrasonic signal; and processing the acquired induced distributed ultrasound signal concurrently detected by the array of ultrasound transducer elements to reconstruct an image.

28. A method for acquiring information on the conductivity distribution in an object, said method comprising the steps of:

applying a magnetic field to said object;

applying an excitation signal along a direction non-parallel to said magnetic field and which induces a local charge displacement in said object as said excitation signal propagates in said object;

acquiring a signal encoded with information indicative of local conductivity of said object for regions along path traversed by said excitation signal, said signal related to an interaction between said magnetic field and said local charge displacement as said excitation signal propagates in said object; and generating an image from said signal, said image weighted by a function of conductivity of said object, said image thereby representing the conductivity distribution of said object.

29. A method for acquiring information on the conductivity distribution in an object, said method comprising the steps of:

applying a magnetic field to said object;

applying an excitation signal along a direction non-parallel to said magnetic field and which induces a local charge displacement in said object as said excitation signal propagates in said object;

acquiring a signal encoded with information indicative of local conductivity of said object for regions along path traversed by said excitation signal, said signal related to an interaction between said magnetic field and said local charge displacement as said excitation signal propagates in said object; and wherein said excitation signal is an acoustic signal localized along a direction of propagation into said object, and said signal is an electrical signal corresponding to a Lorentz interaction between said magnetic field and local displacement of said object as said acoustic signal propagates through said object; and wherein multiple acoustic signals are directed along respective propagation directions into said object, thereby spatially scanning said object with multiple acoustic signals.

30. A method for acquiring information on the conductivity distribution in an object, said method comprising the steps of:

applying a magnetic field to said object;

applying an excitation signal along a direction non-parallel to said magnetic field and which induces a local charge displacement in said object as said excitation signal propagates in said object;

acquiring a signal encoded with information indicative of local conductivity of said object for regions along path traversed by said excitation signal, said signal related to an interaction between said magnetic field and said local charge displacement as said excitation signal propagates in said object;

wherein said excitation signal is a time-varying electrical signal, and said signal is an acoustic signal corresponding to a Lorentz interaction between said magnetic field and local electrical current in said object as said time-varying electrical signal propagates through said object; and wherein said acoustic signal is detected along a given direction, and wherein said given direction is scanned.

31. A method for acquiring information on the conductivity distribution in an object, said method comprising the steps of:

applying a magnetic field to said object;

applying an excitation signal along a direction non-parallel to said magnetic field and which induces a local charge displacement in said object as said excitation signal propagates in said object;

acquiring a signal encoded with information indicative of local conductivity of said object for regions along path traversed by said excitation signal, said signal related to an interaction between said magnetic field and said local charge displacement as said excitation signal propagates in said object;

wherein said excitation signal is a time-varying electrical signal, and said signal is an acoustic signal corresponding to a Lorentz interaction between said magnetic field and local electrical current in said object as said time-varying electrical signal propagates through said object; and wherein said acoustic signal is detected with a transducer which includes an array of elements that concurrently detect acoustic energy respectively localized along respective directions.

32. A system for acquiring information on the conductivity distribution in an object, said system comprising:

a magnet which applies a magnetic field to said object;

means for generating an excitation signal applied along a direction non-parallel to said magnetic field and which induces a local charge displacement in said object as said excitation signal propagates in said object; and means for acquiring a signal encoded with information indicative of local conductivity of said object for regions along path traversed by said excitation signal, said signal related to a Lorentz interaction between said magnetic field and said local charge displacement as said excitation signal propagates in said object; and means for generating an image from said signal, said image weighted by a function of conductivity of said object, said image thereby representing the conductivity distribution of said object.

33. An apparatus for acquiring information on the conductivity distribution in an object, comprising:

an acoustic transducer coupled to said object and which generates an incident acoustic signal that propagates into said object;

a magnetic element that generates a magnetic field in said object;

an electrical signal receiver that receives an electrical signal related to an interaction between said acoustic signal and said magnetic field as said acoustic signal propagates through said object; and a processor that generates an image of said object based on said electrical signal.

34. An apparatus for acquiring information on the conductivity distribution in an object, comprising:

an acoustic transducer coupled to said object and which generates an incident acoustic signal that propagates into said object;

a magnetic element that generates a magnetic field in said object;

an electrical signal receiver that receives an electrical signal related to an interaction between said acoustic signal and said magnetic field as said acoustic signal propagates through said object; and wherein said acoustic transducer generates said acoustic signal as a beam localized along a direction of propagation into said object, and wherein said acoustic transducer generates a series of acoustic signals each directed along a respective propagation direction into said object, thereby spatially scanning said object with the series of acoustic signals.

35. An apparatus for acquiring information on the conductivity distribution in an object, comprising:

a magnetic element that generates a magnetic field in said object;

an electrical signal source that generates a time-varying electrical signal which is applied along a direction non-parallel to said magnetic field and which propagates through said object;

an acoustic transducer coupled to said object and which detects an acoustic signal that propagates through said object and relates to an interaction between said time-varying electrical signal and said magnetic field; and wherein said acoustic transducer detects acoustic energy localized along a given direction, and wherein said given direction is scanned.

36. An apparatus for acquiring information on the conductivity distribution in an object, comprising:

a magnetic element that generates a magnetic field in said object;

an electrical signal source that generates a time-varying electrical signal which is applied along a direction non-parallel to said magnetic field and which propagates through said object;

an acoustic transducer coupled to said object and which detects an acoustic signal that propagates through said object and relates to an interaction between said time-varying electrical signal and said magnetic field; and wherein said acoustic transducer includes an array of elements that concurrently detect acoustic energy from the object.

37. A method for acquiring information applicable for imaging an object based on a spatial function of the conductivity constant and the dielectric constant in the object, said method comprising the steps of:

applying a magnetic field to said object, said object including dielectric properties;

applying an excitation signal along a direction non-parallel to said magnetic field and which induces a local charge displacement in said object as said excitation signal propagates in said object; and acquiring a signal encoded with information that is a spatial function of the local conductivity constant and the local dielectric constant of said object for a plurality of regions along a path traversed by said excitation signal, said signal related to an interaction between said magnetic field and said local charge displacement along the path as said excitation signal propagates in said object.

38. The method according to claim 37, wherein said local charge displacement is capable of being induced in the bulk of said object, and said plurality of regions are capable of being in the bulk of said object.

39. The method according to claim 37, wherein said object is at least a portion of a human body.

\* \* \* \* \*